(12) United States Patent
Zeitsch

(10) Patent No.: US 7,173,142 B2
(45) Date of Patent: Feb. 6, 2007

(54) GASEOUS ACID CATALYSIS

(75) Inventor: Karl J. Zeitsch, deceased, late of Cologne (DE); by Philipp D. Steiner, legal representative, Kwa Zulu Natal (ZA)

(73) Assignee: International Furan Technology (Pty) Limited, Kwa Zulu Natal (ZA)

( * ) Notice: Subject to any disclaimer, the term of this patent is extended or adjusted under 35 U.S.C. 154(b) by 23 days.

(21) Appl. No.: 10/380,417

(22) PCT Filed: Sep. 14, 2001

(86) PCT No.: PCT/ZA01/00146

§ 371 (c)(1),
(2), (4) Date: Sep. 11, 2003

(87) PCT Pub. No.: WO02/22593

PCT Pub. Date: Mar. 21, 2002

(65) Prior Publication Data
US 2004/0068147 A1    Apr. 8, 2004

(30) Foreign Application Priority Data
Sep. 14, 2000  (DE) .............................. 100 45 465

(51) Int. Cl.
C07D 307/48 (2006.01)
C07D 307/50 (2006.01)
(52) U.S. Cl. ...................... 549/489; 549/490
(58) Field of Classification Search ................ 549/489, 549/490
See application file for complete search history.

(56) References Cited

U.S. PATENT DOCUMENTS

| 2,559,607 | A | * | 7/1951 | Dunning et al. | ............ 549/489 |
| 4,001,283 | A |   | 1/1977 | Wells, Jr. | |
| 4,076,733 | A | * | 2/1978 | Dahlgren | ..................... 549/489 |
| 4,154,744 | A |   | 5/1979 | Hamada et al. | |
| 4,533,743 | A | * | 8/1985 | Medeiros et al. | ........... 549/489 |
| 4,912,237 | A | * | 3/1990 | Zeitsch | ...................... 549/489 |

OTHER PUBLICATIONS

Zeitsch, "Gaseous Acid Catalysis: An Intriging New Process", Jan. 2001, Chemical Innovation, vol. 31 No. 1, pp. 4-9.*

* cited by examiner

Primary Examiner—Thomas McKenzie
Assistant Examiner—Raymond Covington
(74) Attorney, Agent, or Firm—Young & Thompson

(57) ABSTRACT

A method of gaseous acid catalysis which finds particular applications in the manufacture of furfural includes the steps of introducing a solid reactant containing one or more hydroxyl groups into a reactor (1); introducing superheated steam from a superheater (2) until the temperature within the reactor (1) is higher than that of the dew points of both water and the catalyst and the reactant is dry. The catalyst is then introduced into the superheated steam by vaporiser (3). Product gas formed is liquified in condenser (4) and the condensate collected in a buffer tank (5). Separation plant isolates the product gas and recovers the acid catalyst, preferably as its azeotrope with water, and recycles it into the vaporiser.

9 Claims, 2 Drawing Sheets

Illustration of a gaseous acid catalysis.

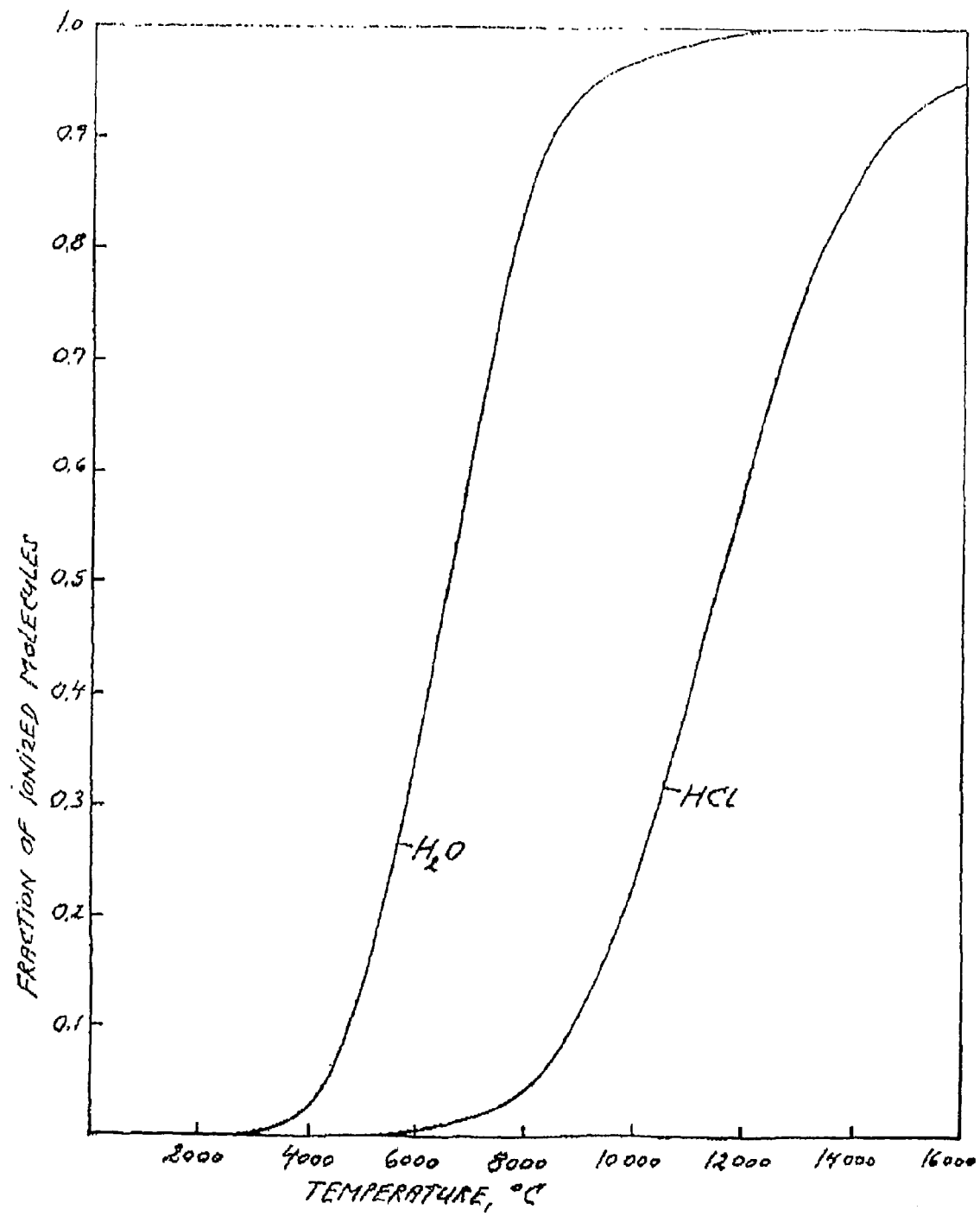
Figure 1. The thermal ionization of water vapor and hydrogen chloride vapor at atmospheric pressure.

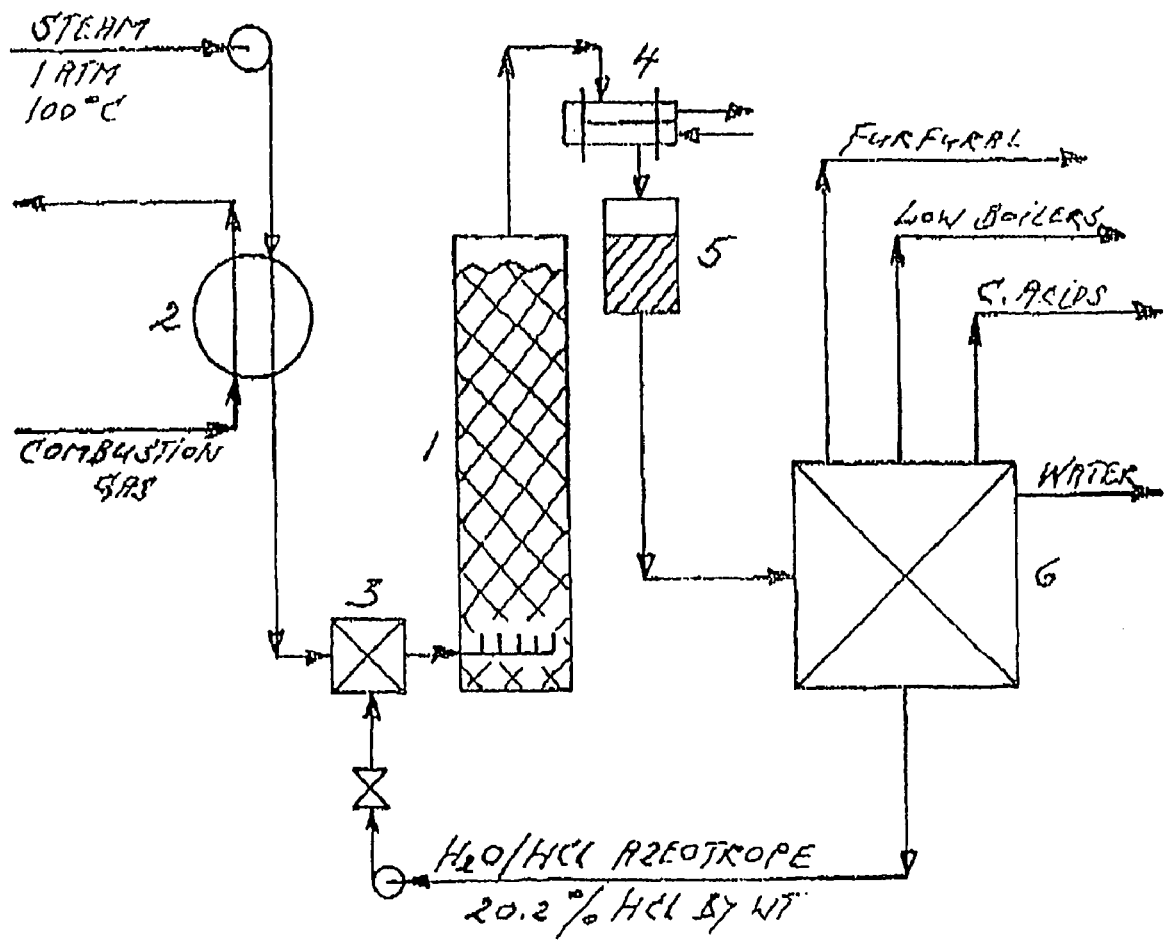
Figure 2. Illustration of a gaseous acid catalysis.

GASEOUS ACID CATALYSIS

TECHNICAL FIELD OF THE INVENTION

This invention relates to gaseous acid catalysis and in particular gaseous acid catalysis of the conversion of pentose or pentosan to furfural.

BACKGROUND ART

Acid catalysis, a common reaction mechanism in organic chemistry, implies the involvement of oxonium, or hydronium, ions, $H_3O+$. "Acid catalysis" is inherently understood to be a process that occurs in aqueous solution. As far as the applicant is aware nobody seems to have used a gas as an acid catalyst, and with good reason. As shown in FIG. 1, gases are not ionized until very high temperatures are reached. As can be seen, there is no significant thermal ionization below 2500° C. for water and below 5000° C. for HCl. Ionization by cosmic rays and ambient radioactivity has also been shown to be negligible, together amounting to no more than 10 ion pairs/(s $cm^3$) with a life span of 70 s. Thus, gases at all but extremely high temperatures may be considered completely nonionized, as demonstrated by their being perfect electrical insulators.

Obviously, a nonionized gas cannot be an "acid catalyst", therefore, it has been the universal belief that acid-catalyzed processes must be carried out in the liquid phase. However, recent studies of stratospheric chemistry and the depletion of the ozone layer have shown that HCl vapour, usually stable, becomes ionized in the presence of ice crystals that are abundant in the stratosphere. HCl and water vapour molecules, are strongly adsorbed on the surface of the ice crystals. In the state of adsorption, each HCl molecules reacts preferentially with four water molecules to form an ionized cluster, $H_3O^+$ $(H_2O)_3Cl^-$, in which the three water molecules form the equatorial plane of a trigonal bipyramid, with $Cl^-$ and $H_3O^+$ ions at the apexes. The chlorine atom carries a charge of $-0.80$ e and the oxonium ion a charge of $+0.85$ e, so that the electrical activity of the cluster is almost equal to that of free $Cl^-$ and $H_3O^+$ ions. The role of the solid surface is to permit HCl molecules to come into contact with four water molecules, which is not possible via collisions in a gas phase devoid of adsorbing surfaces.

It is therefore one object of this invention to provide a method for gaseous acid catalysis.

The applicant has further noted the similarity between ice crystals and other solids having multiple polar hydroxyl groups, for example sugars, and in particular pentose or pentosan.

It is therefore a further object of this invention to provide a method for gaseous acid catalysis catalysed hydrolysis of sugars to form aldehydes and in particular, pentosan and pentose to furfural.

BRIEF DESCRIPTION OF THE DRAWINGS

FIG. 1 shows the thermal ionization of water vapor and hydrogen chloride vapor at atmospheric pressure.

FIG. 2 illustrates a gaseous acid catalysis process.

DISCLOSURE OF THE INVENTION

According to the invention, a method of gaseous acid catalysis includes the steps of introducing a reactant in solid form into a reactor, the reactant including one or more hydroxyl groups; introducing superheated steam into the reactor until the reactant is dry and the temperature within the reactor is above that of the dewpoints of both water and the catalyst to be used; introducing the acid into the reactor together with the superheated steam by means of a vaporiser; and condensing the gas formed.

In the preferred form of the invention, the reactant is capable of forming an ionised cluster complex with water and at least a portion of the acid.

Also in the preferred form, the reaction is carried out at atmospheric pressure. The reactant should be completely dry. In the preferred form, the acid is hydrochloric acid.

In this form of the invention, the reaction must be carried out at a temperature above the boiling point of the maximum $HCl$—$H_2O$ azeotrope. This typically occurs at 20.2 wt % of HCl with a boiling point of 108,6° C. and accordingly the reaction should be carried out above this temperature.

In one form of the invention, the reactant is a sugar.

In one form of the invention, the reactant is pentosan and/or pentose and the solid substance is a comminuted raw material high in pentosan content, for example sunflower stems, corn cobs or bagasse.

DESCRIPTION OF AN EXAMPLE OF THE INVENTION

A typical gaseous acid catalysis process using hydrochloric acid is illustrated in FIG. 2. Reactor 1 is charged with comminuted raw material of high pentosan content, such as sunflower stems, corncobs, or bagasse. Steam at atmospheric pressure is passed through a superheater 2 typically fuelled by combustion gas, and this stream is then passed through the charge to first completely dry the charge and then heat it to a temperature far above the maximum atmospheric dew point of hydrochloric acid. The charge will heat rapidly once the moisture has been stripped from it. When the desired temperature is reached, a small quantity of hydrochloric acid is continuously dispersed into the superheated stem by means of a vaporizer 3 to give the gas stream an HCl content of approximately 1.5 wt %. The gas stream leaving the reactor is liquefied in a condenser 4, and the condensate is collected in a buffer tank 5 before it enters a separation plant 6 that isolates furfural, low boiling compounds, and carboxylic acids and recovers HCl as its azerotrope with water. This hydrochloric acid is used to feed the vaporiser 3, so that the catalyst is contained in a closed circuit. The "pervaporisation" of the charge is continued until no more furfural is produced. Then, the residue is discharged under nitrogen, to prevent self-ignition, and a new batch is started.

When this reaction is carried out at 155° C., the applicant found that the existing gas stream was heavily loaded with furfural, low boiling compounds and carboxylic acids.

What is most surprising about this result is the presence of the furfural as a gas even though the process is carried out at a temperature below its boiling point (161.7° C.).

An important advantage of this new process is that the absence of a liquid phase greatly increases the furfural yield. In convention furfural process, the furfural generated dissolves in the liquid phase, where, under the catalyzing influence of oxonium ions, it undergoes loss reactions with itself and with intermediates of the pentose-to-furfural conversion. In addition, with sulphuric acid as the customary catalyst, there are losses by sulfontation. Consequently, the yield in conventional furfural plants is only on the order of 50%. By contrast, in gaseous acid catalysis, with no liquid phase in which to dissolve, the generated furfural is instantly vaporised and loss reactions are avoided.

In a laboratory test, yields of the order of 95% have been achieved.

In conventional furfural processing, high pressures are needed to keep the aqueous catalyst in the liquid state, and the customary catalyst, sulphuric acid, is nonvolatile, so that it is lost in the residue where it presents a disposal problem.

As compared to this conventional processing, the new gaseous catalysis process has the following advantages:

1 At any chosen temperature, the process can be carried out at atmospheric pressure.
2. As the $H_2O/HCl$ catalyst is used far above its dew point, there is no corrosion, so that the reactor can be made of mild steel.
3. The acid portion of the catalyst can be completely recovered, to be run in a closed circuit, so that there is no acid consumption and no acid disposal problem. Known technology is available for the acid recovery.
4. The residue is dry and free of acid, thus being eminently suited for a simple combustion without any problems. By partial combustion in air, it is also possible to use the residue for the manufacture of "producer gas" consisting mostly of carbon monoxide, hydrogen and nitrogen.
5. The yield is close to 100 percent as there is no liquid phase where loss reactions could take place. Yields of up to 95.8 percent have been measured.

It should be noted that although an example of a batch process is described hereinabove, the applicant submits that a continuous process may be used.

The invention claimed is:

1. A process for the manufacture of aldehydes from sugars where in the hydrolysis of the sugar is catalysed by introducing a reactant in solid form into a reactor, the reactant containing one or more sugars; introducing superheated steam into the reactor until the reactant is dry and the temperature within the reactor is above that of the dewpoints of both water and the catalyst to be used; introducing the acid together with the superheated steam into the reactor by means of a vaporiser; and condensing the gas formed.

2. The process for the manufacture of aldehydes from sugars according to claim 1 wherein the reaction is carried out at a temperature above the boiling point of the maximum $HCl—H_2O$ azeotrope.

3. A process for the manufacture of furfural from pentosan wherein the hydrolysis of pentosan and/or pentose and subsequent dehydrate to furfural is catalysed by gaseous hydrochloric acid according to the method of claim 1.

4. The process for the manufacture of furfural according to claim 3 wherein the hydrochloric acid is recycled as its azeotrope with water.

5. The process for the manufacture of furfural according to claim 3 wherein the reaction is carried out at a temperature above the boiling point of the maximum $HCl—H_2O$ azeotrope.

6. The process for the manufacture of furfural according to claim 3 wherein the reaction is carried out at 155° C.

7. The process for the manufacture of furfural according to claim 3 wherein the yield of furfural is greater than 90%.

8. The process according to claim 3 wherein said process is continuous.

9. The process according to claim 3 wherein the reaction is carried out at atmospheric pressure.

* * * * *